United States Patent
Hall et al.

(10) Patent No.: US 10,792,069 B2
(45) Date of Patent: Oct. 6, 2020

(54) TROCAR SEAL ASSEMBLIES

(71) Applicant: Ethicon LLC, Guaynabo, PR (US)

(72) Inventors: Steven G. Hall, Lebanon, OH (US); Katherine J. Schmid, Cincinnati, OH (US); Joe Mozloom, Cincinnati, OH (US); Harry Adams, Fort Thomas, KY (US)

(73) Assignee: Ethicon LLC, Guaynabo, PR (US)

( * ) Notice: Subject to any disclaimer, the term of this patent is extended or adjusted under 35 U.S.C. 154(b) by 199 days.

(21) Appl. No.: 15/715,864

(22) Filed: Sep. 26, 2017

(65) Prior Publication Data

US 2019/0090905 A1 Mar. 28, 2019

(51) Int. Cl.
*A61B 17/34* (2006.01)

(52) U.S. Cl.
CPC ...... *A61B 17/3462* (2013.01); *A61B 17/3474* (2013.01); *A61B 17/3498* (2013.01); *A61B 2017/3419* (2013.01); *A61B 2017/3464* (2013.01); *A61B 2017/3466* (2013.01)

(58) Field of Classification Search
CPC ............ A61B 17/3462; A61B 17/3474; A61B 17/3498; A61B 2017/3419; A61B 2017/3464; A61B 2017/3466; A61B 2017/3441
USPC ........................................ 604/167.01–167.04
See application file for complete search history.

(56) References Cited

U.S. PATENT DOCUMENTS

| | | | |
|---|---|---|---|
| 5,458,640 A * | 10/1995 | Gerrone | A61B 17/3417 604/158 |
| 5,895,377 A | 4/1999 | Smith et al. | |
| 7,833,199 B2 * | 11/2010 | Franer | A61B 17/3462 604/167.03 |
| 2006/0217665 A1 | 9/2006 | Prosek | |
| 2009/0030375 A1 | 1/2009 | Franer et al. | |
| 2009/0076456 A1 | 3/2009 | Armstrong et al. | |
| 2012/0116313 A1 | 5/2012 | Franer et al. | |
| 2014/0088491 A1 * | 3/2014 | Azarbarzin | A61B 17/3421 604/26 |

(Continued)

FOREIGN PATENT DOCUMENTS

WO 0162167 A1 8/2001

OTHER PUBLICATIONS

ISRWO of corresponding PCT/IB2018/057299 dated Aug. 1, 2019.

*Primary Examiner* — Kami A Bosworth
*Assistant Examiner* — Leah J Swanson
(74) *Attorney, Agent, or Firm* — Vorys, Sater, Seymour and Pease LLP (57) ABSTRACT

A trocar assembly includes a seal assembly that maintains insufflation pressure when sized seal cartridges are removed and replaced. The trocar assembly includes a housing that defines a working chamber, and a cannula distally extends from the housing and defines a lumen that communicates with the working chamber. The seal cartridge is arranged within the working chamber, and may include one or both of a proximal seal assembly and a distal seal assembly arranged distally from the proximal seal assembly, and may further include a bushing extending distally from a distal end of the seal cartridge and into the lumen. A tertiary seal may also be positioned within the working chamber distal to the seal cartridge, such that the bushing extends through the tertiary seal when the seal cartridge is received within the working chamber.

20 Claims, 6 Drawing Sheets

(56) References Cited

U.S. PATENT DOCUMENTS

2015/0305863 A1\* 10/2015 Gray ..................... A61F 2/962
623/2.11

\* cited by examiner

TROCAR SEAL ASSEMBLIES

BACKGROUND

During laparoscopic surgery, one or more small incisions are formed in the skin of patient and a trocar assembly is inserted through the incision to form a pathway that provides access to an internal body cavity, such as the patient's abdomen. The trocar assembly is used to introduce various instruments and tools into the body cavity, as well as to provide insufflation to elevate interior walls of the body cavity. During such procedures, a scoping device, such as an endoscope or laparoscope, can be inserted through the trocar assembly and into the body cavity to allow a surgeon to view the operative field on an external monitor coupled to the scoping device.

A trocar assembly generally includes a cannula, an obturator, and a housing. In order to access the body cavity, the cannula is directed through the skin and the obturator is inserted through an interior lumen defined by the cannula to provide penetration access to the body cavity. The cannula is then inserted through the perforation made by the obturator and the obturator is withdrawn, leaving the interior lumen of the cannula as a path to access the body cavity from outside the body. The trocar housing is attached to the proximal end of the cannula and defines a working chamber with an open distal end in communication with the interior lumen of the cannula. Just as the interior lumen can receive the obturator, it can also receive other elongated surgical instruments that are axially extended into and withdrawn from the cannula through the proximal end portion of the working chamber.

In robotic surgery incorporating trocar assemblies, surgical instruments having two or more different diameters can be used. The diameter of the trocar assembly is typically determined based on the diameter of the surgical instrument to be used. For example, a 12 mm trocar assembly will be used to enable a 12 mm surgical instrument (e.g., a surgical stapler) to be used. For some procedures, however, an 8 mm surgical instrument may be required to pass through the 12 mm trocar assembly.

A seal assembly or sealing device is commonly incorporated in the trocar assembly to help prevent fluid or gas from escaping during surgical procedures. Such prevention is needed, especially during certain minimally invasive surgical procedures in which an insufflation gas is used to expand the body cavity. The seal assembly operates to seal against the outer surface of inserted instruments and thus prevents fluids and insufflation gas from escaping and/or entering the body cavity through the cannula.

Some trocar seal assemblies include removable seal cartridges designed to accommodate surgical instruments of a particular outer diameter. When a surgical instrument of a different diameter is required, however, the seal cartridge is removed from the trocar housing and replaced with a different seal cartridge capable of accommodating the different diameter. While swapping out a seal cartridge for a properly sized seal cartridge, the insufflation in the body cavity needs to be maintained.

This presents a challenge in robotic surgery since surgical robots "drive" or locate the surgical instrument by rotating the trocar assembly around intra-abdominally. When a surgical instrument of a smaller diameter is used in a larger diameter trocar assembly (e.g., an 8 mm surgical instrument used in a 12 mm trocar assembly) there is "lost motion" or hysteresis to the movement. The initial movement input to the robot by the surgeon will not move the surgical instrument, but will instead first remove the clearance between the instrument and the trocar assembly, and will subsequently move the surgical instrument. This lost motion is unacceptable to the surgeon, who expects fine control and precision from the surgical robot.

The clearance between the trocar assembly and the smaller diameter surgical instrument can also result in the surgical instrument vibrating without hitting the inner walls of the trocar assembly. If an 8 mm surgical instrument is used in the same size 8 mm trocar assembly, this vibration is dampened by the instrument hitting the inner walls of the trocar assembly, but in the case of an 8 mm surgical instrument being used in a 12 mm trocar assembly, this vibration can occur undampened.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to trocar assemblies and, more particularly, to seal assemblies that can be used in robotic trocar assemblies.

The embodiments described herein provide a trocar assembly with an integral seal that helps maintain insufflation pressure when removing and replacing a seal cartridge. Other embodiments described herein provide seal cartridges utilizable in a trocar assembly that include a telescoping bushing and/or sleeve that may operate to reduce the inner diameter of the trocar cannula lumen and thus help eliminate or minimize unintended movement and vibration of smaller surgical tools.

Figure 1:
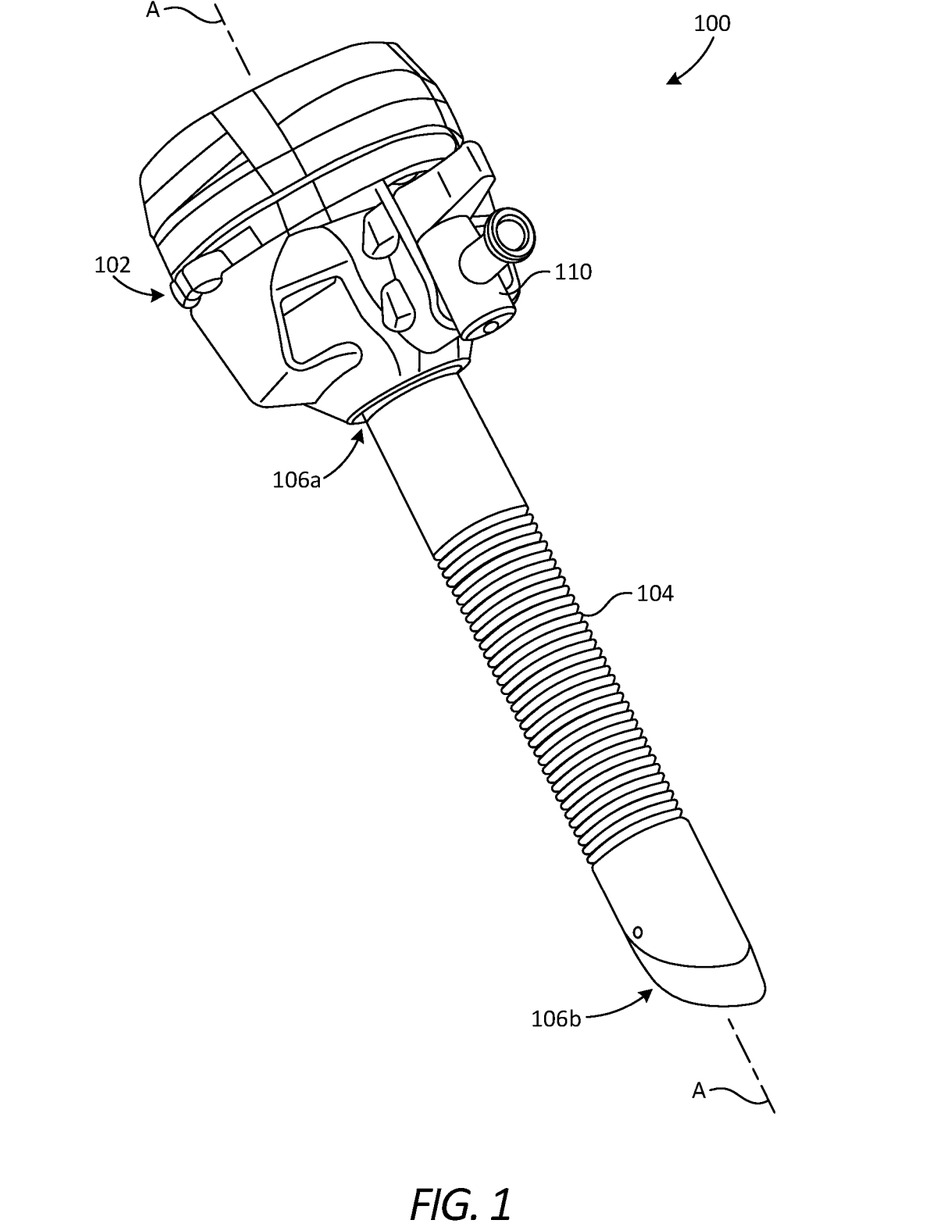
FIG. 1 is an isometric view of an example trocar assembly that may incorporate the principles of the present disclosure.

FIG. 1 is an isometric view of an example trocar assembly 100 that may incorporate the principles of the present disclosure. The depicted trocar assembly 100 is just one example trocar assembly that can suitably incorporate the principles of the present disclosure. Indeed, many alternative designs and configurations of the trocar assembly 100 may be employed, without departing from the scope of this disclosure.

As illustrated, the trocar assembly 100 includes a trocar housing 102 and a cannula 104, and the cannula 104 has a proximal end 106a and a distal end 106b. The cannula 104 is coupled to the trocar housing 102 at the proximal end 106a and extends distally therefrom. In some embodiments, the cannula 104 may comprise an integral extension of the trocar housing 102. In other embodiments, however, the trocar housing 102 and the cannula 104 may comprise two separate components that may be mated to one another. The trocar housing 102 and cannula 104 may be made of any rigid or semi-rigid material, such as a metal or a plastic.

The trocar assembly 100 may also include an insufflation valve 110 (e.g., a stopcock valve) coupled to the trocar housing 102 or forming an integral part thereof. The insufflation valve 110 is operable to introduce an insufflation fluid (e.g. carbon dioxide) through the trocar housing 102 and the cannula 104 and subsequently into an inner cavity (e.g., the abdomen) of a patient to elevate the interior walls of the inner cavity thereby creating more work room. While not shown, the trocar assembly 100 may also include an obturator extendable through the trocar assembly along a centerline A of the trocar assembly 100. When used, the obturator extends through the cannula 104 and out the distal end 106b to penetrate a patient's skin and thereby facilitate access to the abdominal cavity.

Figure 2:
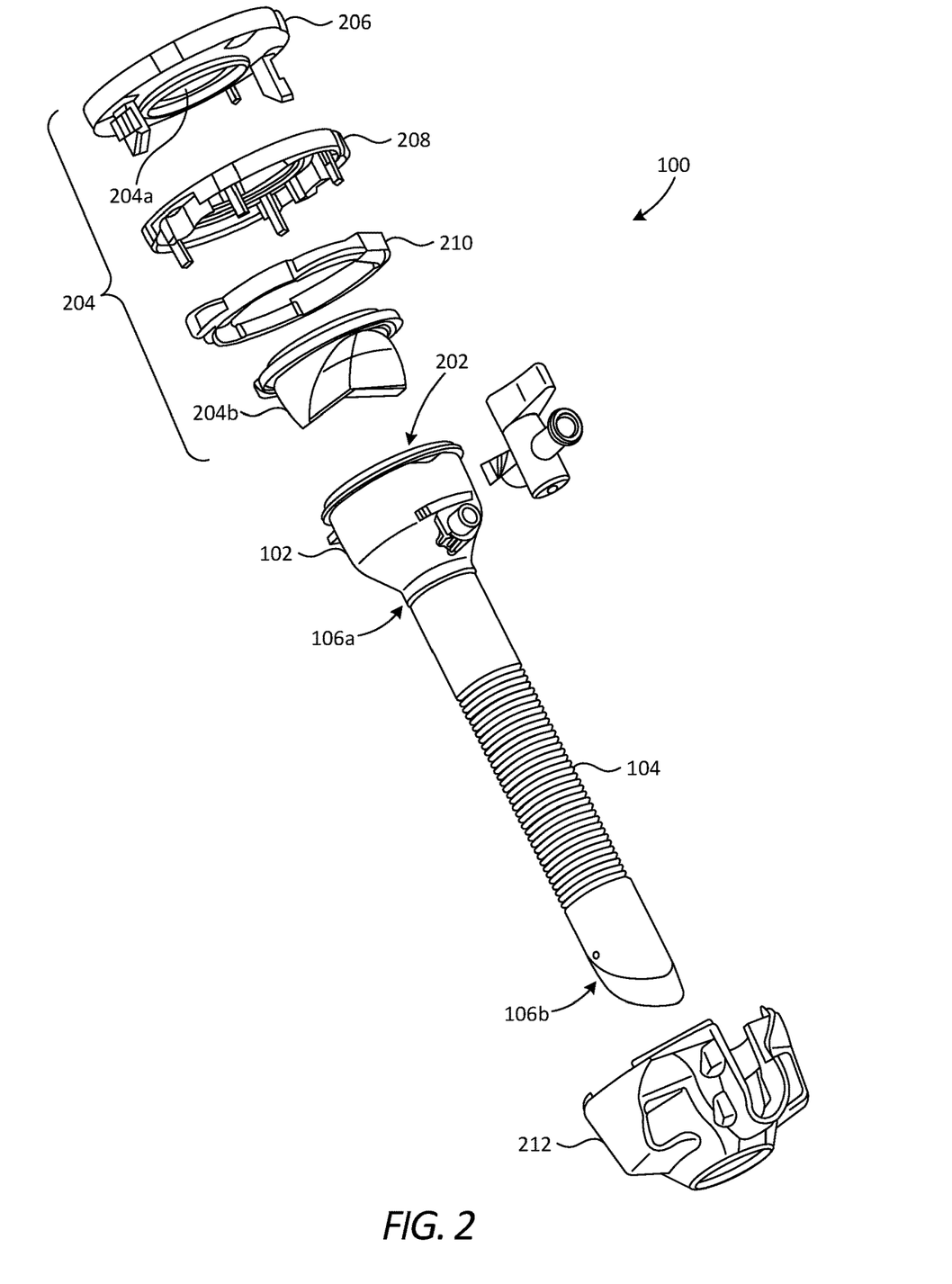
FIG. 2 is an exploded view of the trocar assembly of FIG. 1.

FIG. 2 is an exploded view of the trocar assembly 100 of FIG. 1. The trocar housing 102 provides and otherwise defines a working chamber 202 that communicates with a lumen defined within the cannula 104. The lumen is open-ended and extends between the proximal and distal ends 106a,b of the cannula 104.

The working chamber 202 is also open-ended and configured to at least partially receive a seal cartridge 204 that includes a first or "proximal" seal assembly 204a and a second or "distal" seal assembly 204b. The first and second seal assemblies 204a,b allow selective sealing of the working chamber 202 during operation. In at least one embodiment, as illustrated, the second seal assembly 204b may comprise a duckbill seal. While two seal assemblies 204a,b are depicted in FIG. 2, the seal cartridge 204 may alternatively include more or less than two seal assemblies, without departing from the scope of the disclosure.

The seal assemblies 204a,b may be made of an elastic or pliable material, and suitable elastic or pliable materials include, but are not limited to, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), silicone, ethylene vinyl acetate, nylon, vinyl, spandex, polyurethane, polyethylene, polypropylene, polyisoprene, or any combination thereof. Example seal cartridges are described in U.S. Pat. No. 8,771,307, the contents of which are hereby incorporated by reference.

The seal cartridge 204 may be assembled in a variety of ways. In the illustrated embodiment, for example, a crown ring 206 and a gasket ring 208 may be snap-fit together, and a gasket retainer ring 210 may be configured to secure an attachment between the gasket ring 208 and the trocar housing 102. A housing retainer 212 may then be extended about the exterior of the trocar housing 102 to secure the internal components to the trocar housing 102. These components may be made of any rigid or semi-rigid material, such as a metal or a plastic.

Figure 3:
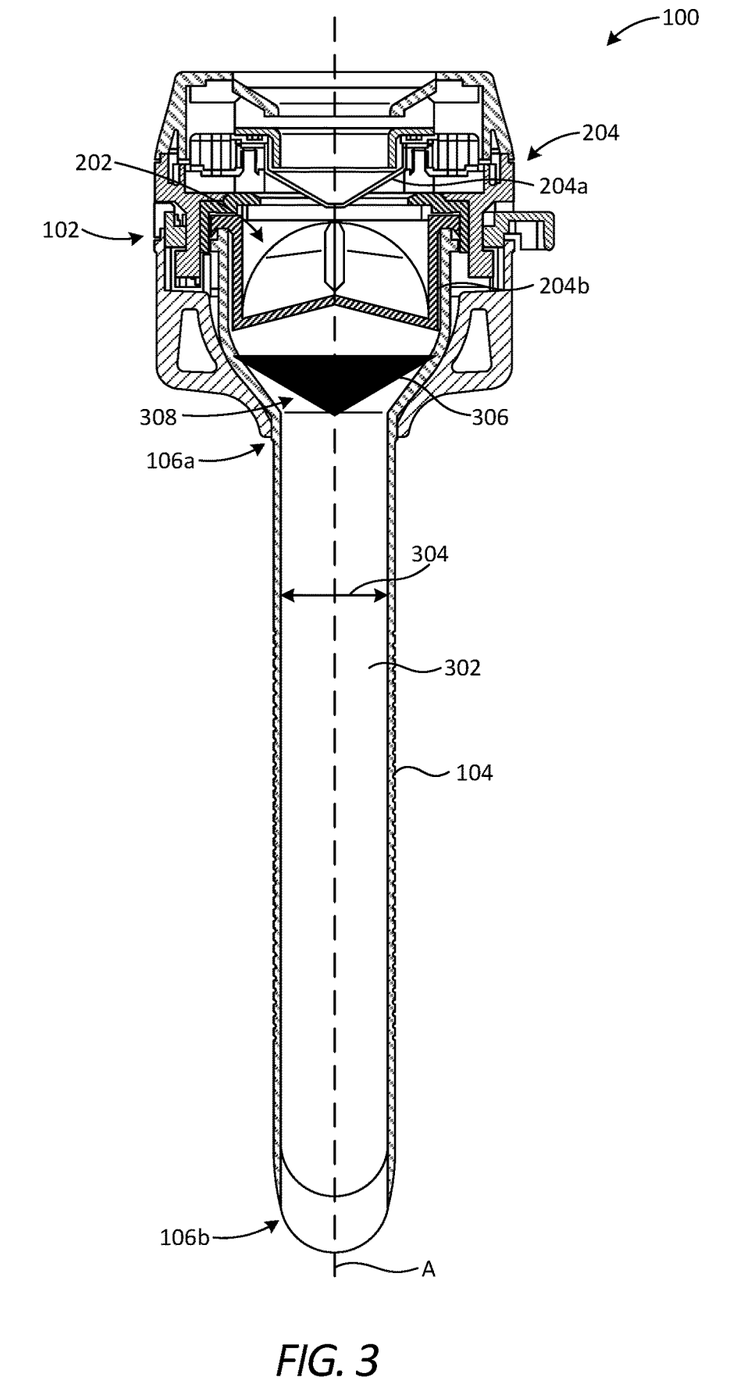
FIG. 3 is a cross-sectional side view of the trocar assembly of FIG. 1.

FIG. 3 is a cross-sectional side view of the trocar assembly 100. As illustrated, the cannula 104 defines and otherwise provides a lumen 302 that extends between the proximal and distal ends 106a,b and communicates with the working chamber 202 provided by the trocar housing 102. The lumen 302 exhibits an inner diameter 304 configured to receive surgical tools having an outer diameter equal to (i.e., slightly less than equal) or less than the inner diameter 304.

According to embodiments of the present disclosure, an additional or tertiary seal 306 may be incorporated into the trocar assembly 100 at or near a distal end or region 308 of the working chamber 202. The tertiary seal 306 may alternately be referred to as a "distal seal," as the first and second seal assemblies 204a,b may alternately be referred to as a "proximal seal" and a medial seal," respectively. The tertiary seal 306 may prove advantageous in maintaining insufflation pressure when a surgical tool and/or seal cartridge such as seal cartridge 204 is removed from the trocar assembly 100 and replaced with a different tool and/or seal cartridge. In the illustrated embodiment, the tertiary seal 306 is disposed within the distal region 308 of the working chamber 202 and distally located from the second seal assembly 204b. In other embodiments, however, the tertiary seal 306 may be arranged in other locations within the working chamber 202, without departing from the scope of the disclosure.

Figure 4:
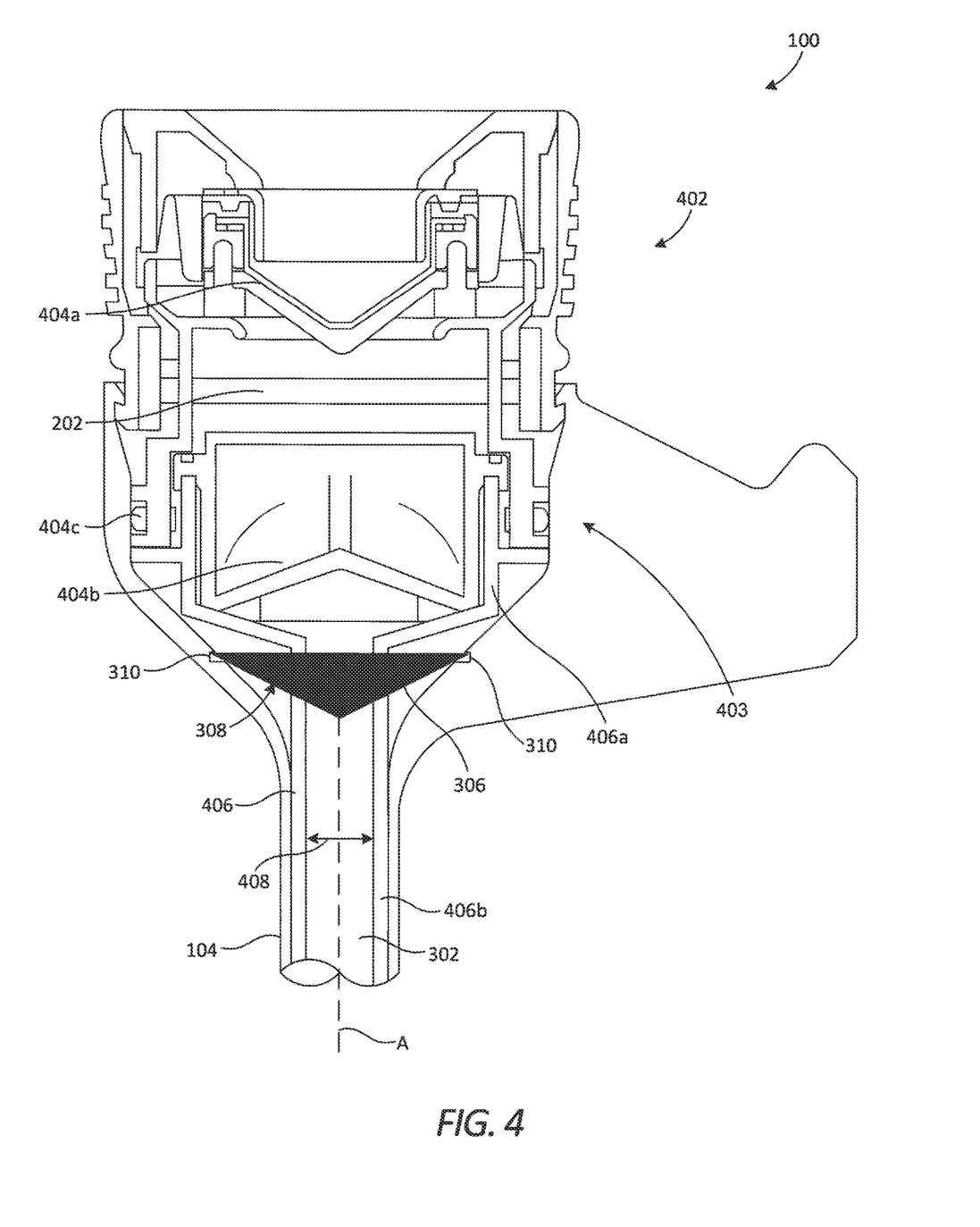
FIG. 4 is a cross-sectional side view of an alternate seal cartridge embodiment installed within the trocar assembly of FIGS. 1-3.

In one or more embodiments, the tertiary seal 306 is coupled to (integral with) the trocar housing 102 so that it remains in place within the working chamber 202 to maintain insufflation pressure. In at least one embodiment, the tertiary seal 306 is mounted within an annular ring or groove 310 formed in the inner surface of the working chamber 202 as illustrated in FIG. 4. In other embodiments, the tertiary seal 306 is secured within the working chamber via an attachment means selected from the group consisting of one or more mechanical fasteners, a threaded engagement, welding, ultrasonic welding, brazing, an adhesive, an interference fit, a shrink fit, a mechanical attachment, and any combination thereof.

The tertiary seal 306 may comprise a variety of different types and configurations of seals capable of providing a sealed interface at the distal region 308 of the working chamber 202. In at least one embodiment, the tertiary seal 306 may comprise a pass-through seal, such as a duckbill seal. Additionally, the tertiary seal 306 may be made of a pliable or elastic material including those mentioned herein with respect to the seal assemblies 204a,b of FIGS. 2-3.

As mentioned above, the lumen 302 exhibits an inner diameter 304 configured to receive surgical tools having an outer diameter less than or equal to the inner diameter 304. In at least one embodiment, the inner diameter 304 may be sized to receive a 12 mm surgical tool. In such embodiments, the trocar assembly 100 may be referred to and otherwise characterized as a "12 mm trocar," which is commonly used in robotic surgery to accommodate various 12 mm surgical tools, such as surgical staplers. In other embodiments, however, the inner diameter 304 may be differently sized (e.g., 8 mm, 5 mm, etc.). As a surgical tool is extended into the trocar assembly 100, the first and second seal assemblies 204a,b and the tertiary seal 306 are configured to deform and provide a sealed interface against the outer surface of the surgical tool.

Where a surgical tool exhibits an outer diameter that is approximately equal to the inner diameter 304, the surgical tool will be generally centered within the cannula 104 along the centerline A at all times, which tends to mitigate unwanted occurrences of deflection, oscillation, and vibration of the surgical tool. Accordingly, where a 12 mm surgical tool is inserted through a 12 mm trocar, the outer surface of the surgical tool will contact or be in close contact with the inner surface of the lumen 302 such that very little clearance remains between the surgical tool and the inner wall of the lumen 302. As a result, the surgical tool may be generally centered within the lumen 302, which mitigates deflection, oscillation, and vibration.

At times, however, surgical tools exhibiting outer diameters that are smaller than the inner diameter 304 (i.e., a smaller surgical tool) may need to be introduced into the trocar assembly 100. In some applications, for example, the outer diameter of a smaller surgical tool may be approximately 8 mm (i.e., an "8 mm surgical tool") or approximately 5 mm (i.e., a "5 mm surgical tool"). As the smaller surgical tool is extended into the trocar assembly 100, the first and second seal assemblies 204a,b and tertiary seal 306 are configured to deform and provide a sealed interface against the outer surface of such smaller surgical tool. The seal assemblies 204a,b and the tertiary seal 306 each helps maintain insufflation during various operations undertaken and while pulling the smaller surgical tool out of the cannula 104.

However, since the outer diameter of the smaller surgical tool is smaller than the inner diameter 304 of the lumen 302, the smaller surgical tool will rarely (if ever) be centered within the cannula 104 along the centerline A during operation. Rather, the smaller surgical tool will continuously be prone to deflection, oscillation in place, spring back oscillation, and vibration as it is manipulated in various directions during operation.

According to embodiments of the present disclosure, a sleeve or bushing may be incorporated into the trocar assembly 100 and extend distally from the seal cartridge 204 at or near a distal end thereof into the lumen 302. In such embodiments, the sleeve or bushing may operate as a reducer that accommodates smaller-diameter surgical tools and eliminates or significantly minimizes unintended movement and vibration of smaller surgical tools when fed through a lumen 302 having a larger inner diameter 304.

FIG. 4 is a cross-sectional side view of an example seal cartridge 402 that may be utilized with the trocar assembly 100 of FIGS. 1-3, according to one or more embodiments of the present disclosure. As illustrated, the seal cartridge 402 is at least partially arrangeable within the working chamber 202.

The seal cartridge 402 may be similar to the seal cartridge 204 depicted in FIGS. 2-3 in that the seal cartridge 402 may include a first or "proximal" seal assembly 404a and a second or "distal" seal assembly 404b. While two seal assemblies 404a,b are depicted in FIG. 4, the seal cartridge 402 may alternatively include more or less than two seal assemblies to allow selective sealing of the working chamber 202 during operation, without departing from the scope of the disclosure.

In addition, the first and second seal assemblies 404a,b may be assembled and secured within seal cartridge 402 in a similar manner as utilized with respect to the seal cartridge 204 of FIGS. 2-3. Moreover, the first and second seal assemblies 404a,b may be made of a pliable or elastic material including those mentioned herein with respect to the seal assemblies 204a,b of FIGS. 2-3. In some embodiments, seal cartridge 402 may further comprise an auxiliary seal or gasket 404c, such as an O-ring or the like, that ensures a sealed interface between the periphery of the seal cartridge 402 and the inner wall of the working chamber 202. The auxiliary seal 404c may also be made of a pliable or elastic material including those mentioned herein with respect to the seal assemblies 204a,b of FIGS. 2-3.

The seal cartridge 402 may also include, however, a sleeve or bushing 406. In the illustrated embodiment, the bushing 406 is mounted or secured to a distal end 403 of the seal cartridge 402, and the bushing 406 distally extends therefrom into and through the lumen 302 of the cannula 104. In some embodiments, the bushing 406 extends through the entire length of the lumen 302 along centerline A, whereas in other embodiments the bushing 406 may terminate before the end of the lumen 302.

Various attachment means may be utilized to mount or secure the bushing 406 to the seal cartridge 402, including the use of one or more mechanical fasteners, a threaded engagement, welding, ultrasonic welding, brazing, an adhesive, an interference fit, a shrink fit, a mechanical attachment, and any combination thereof.

The bushing 406 includes a proximal portion 406a and a distal portion 406b that extends distally from the proximal portion 406a. In the illustrated embodiment, the proximal portion 406a is configured to be arranged within the distal region 308 of working chamber 202 when the seal cartridge 402 is installed and, in some embodiments, the proximal portion 406a is further configured to receive a seal assembly such as the second seal assembly 404b. For example, the proximal portion 406a may comprise a frustoconical portion or surface that connects to the distal portion 406b, and the frustoconical portion may be adapted to receive the second seal assembly 404b. Also in the illustrated embodiment, the distal portion 406b is configured to be received within the lumen 302 of the cannula 104. Therefore, it will be appreciated that the proximal portion 406a may operate as a "reducer" that effectively reduces the inner diameter 304 of the lumen 302 to a reduced inner diameter 408 of the distal portion 406b.

The reduced inner diameter 408 may be sized to match the outer diameter of a smaller surgical tool inserted therethrough (not illustrated) so that the smaller surgical tool will not oscillate or vibrate when utilized in conjunction with the trocar assembly 100. For example, the inner diameter 408 may be approximately 5 mm or 8 mm in diameter to receive 5 mm surgical tools or 8 mm surgical tools, respectively. However, in other embodiments the reduced inner diameter 408 may still be larger than the outer diameter of the smaller surgical tool. In such embodiments, the smaller surgical tool will experience less unintended movement and/or vibration due to the reduced inner diameter 408 of the bushing 406 than would be experienced in applications without bushing 406.

With reference to FIGS. 3 and 4, during operation, an internal body cavity (e.g., a patient's abdomen) will be pressurized or insufflated using the trocar assembly 100 to provide access for an operator or a surgeon. Once the cavity has been insufflated, the operator or surgeon may insert the seal cartridge 204 into the trocar assembly 100 to utilize a large surgical tool such as a 12 mm surgical tool. Situations may arise, however, where the operator or surgeon needs to utilize a smaller surgical tool such as an 8 mm or 5 mm surgical tool. In such situations, the operator or surgeon may remove the 12 mm surgical tool from the trocar assembly 100, and may then remove the first seal cartridge 204 from the trocar assembly 100 in preparation for installing the second seal cartridge 402, which includes the smaller diameter bushing 406.

While removing the first seal cartridge 204 and installing the second seal cartridge 402, insufflation pressure is maintained due to the presence of the tertiary seal 306 positioned within the distal region 308 of working chamber 202. Installing the second seal cartridge 402 within the working chamber 202 includes inserting or penetrating the tertiary seal 306 with the distal portion 406b of the bushing 406 and introducing the distal portion 406b into the lumen 302. Once the operator or surgeon has installed the seal cartridge 402, the smaller surgical tool may then be extended into the trocar assembly 100 and through the reduced inner diameter 408 of the bushing 406.

When no longer required, the smaller surgical tool may be removed from the trocar assembly 100 and the second seal cartridge 402 may then be removed from the working chamber 202. During this process, insufflation pressure is still maintained, even with the bushing 406 still penetrating the tertiary seal 306 during removal, due to the presence of the second seal assembly 404b that is not penetrated by the smaller surgical tool and thus fully engaged or closed to maintain insufflation pressure.

Figure 5A:
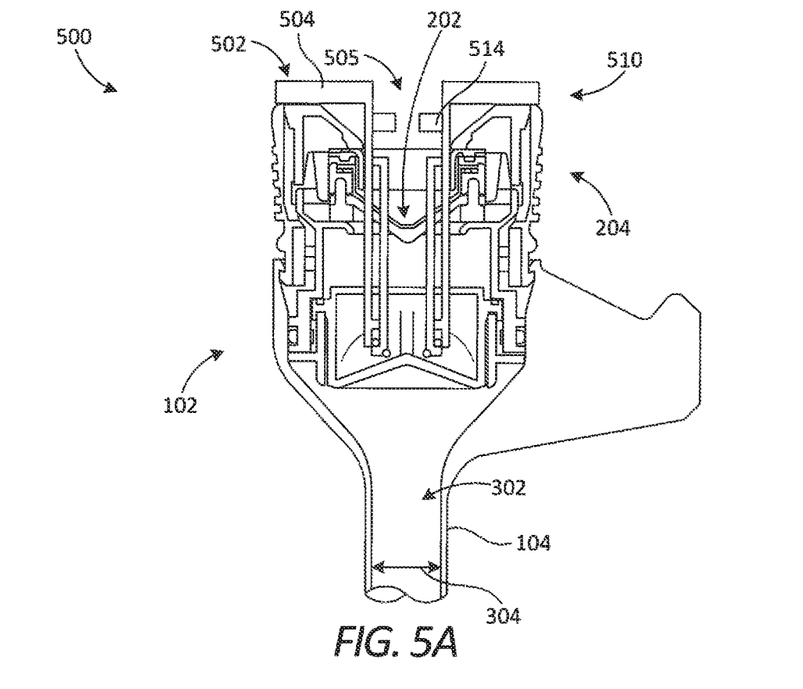
FIGS. 5A and 5B are cross-sectional side views of a telescoping bushing assembly installed within the trocar assembly of FIGS. 1-3.
Figure 5B:
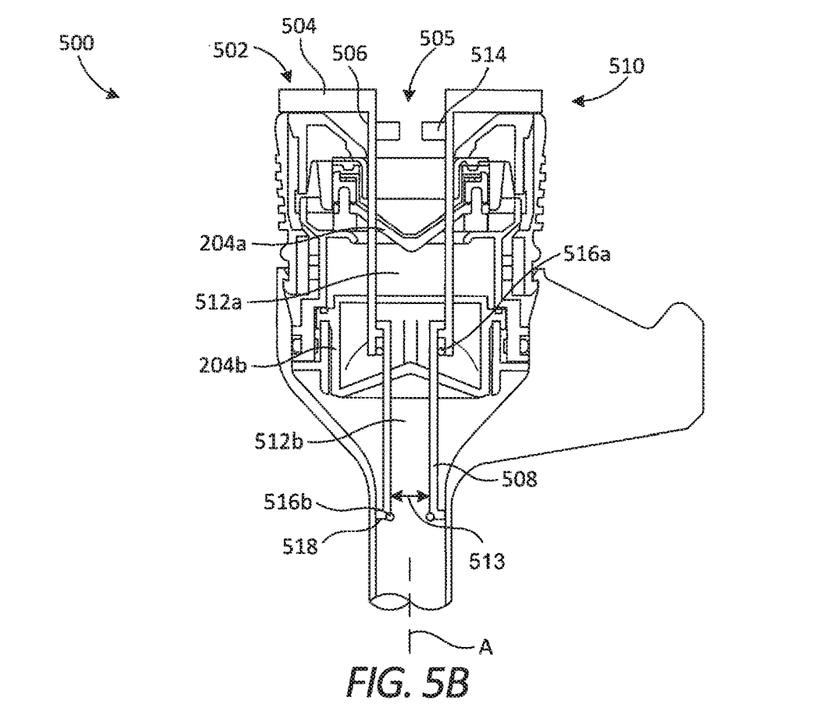

FIGS. 5A and 5B are cross-sectional side views of another example trocar assembly 500, according to one or more additional embodiments of the present disclosure. The trocar assembly 500 may be similar in some respects to the trocar assembly 100 of FIGS. 1-3, where like numerals refer to similar components that may not be described in detail again. Similar to the trocar assembly 100 of FIGS. 1-3, the trocar assembly 500 includes the cannula 104 extending distally from the housing 102 and defining the lumen 302. The trocar assembly 500 also includes the proximal and distal seal assemblies 204a,b of the seal cartridge 204.

Unlike the trocar assembly 100 of FIGS. 1-3, however, the trocar assembly 500 further includes a telescoping bushing assembly 502. As illustrated, the telescoping bushing assembly 502 is at least partially arrangeable within the working chamber 202, and includes a ring 504, a sleeve 506 that extends distally from the ring 504, and a bushing 508 that is configured to translate or "telescope" within and relative to the sleeve 506. Various attachment means may be utilized to mount or secure the sleeve 506 to the ring 504, including the use of one or more mechanical fasteners, a threaded engagement, welding, ultrasonic welding, brazing, an adhesive, an interference fit, a shrink fit, a mechanical attachment, and any combination thereof. Moreover, the ring 504, the sleeve 506, and the bushing 508 may be made from any rigid or semi-rigid material like plastic or metal.

In the illustrated embodiment, the ring 504 is annular with an opening 505 configured to receive a surgical tool and is disposed on a proximal end 510 of the trocar assembly 100 and seal cartridge 204. In some embodiments, the ring 504 may be secured to the proximal end 510 of the trocar assembly 100. For example, suitable locking mechanisms may include, without limitation, a threaded engagement, one or more clips, one or more latches, a friction locking assembly, and any combination thereof. In other embodiments, however, the ring 504 may simply rest on the proximal end 510 of the trocar assembly 100, without departing from the scope of the disclosure.

The sleeve 506 extends distally from the ring 504 and defines a channel or pathway 512a through which a surgical tool may be inserted. The bushing 508 also defines a channel or pathway 512b that communicates with the pathway 512a and through which a surgical tool may be inserted. The pathway 512b of the bushing 508 defines a diameter 513 that will be approximately equal to the diameter of the surgical tool inserted therethrough, though in some embodiments surgical tools having shafts smaller than the diameter 513 may be utilized therein. In these configuration, the smaller surgical tool will be generally centered within the cannula 104 along the centerline A at all times, which tends to mitigate unwanted occurrences of deflection, oscillation, and vibration of the surgical tool.

The bushing 508 also defines an outer diameter that is approximately equal to the inner diameter 304 of lumen 302. In some embodiments, however, the bushing 508 defines an outer diameter that is less than the inner diameter 304 of lumen 302. In such embodiments, the bushing 508 includes one or more flanges 518 (one shown) that radially extend from the periphery of the bushing 508 to abut or contact the inner wall of the lumen 302, and thereby centering the bushing 508 within the lumen 302. In one embodiment, the flange 518 may be an annular flange extending around the perimeter of the distal end of the bushing 508 and has an outer diameter approximately equal to the inner diameter 304 of the lumen 302.

The telescoping bushing assembly 502 is movable between a retracted configuration, as shown in FIG. 5A, and an extended configuration, as shown in FIG. 5B. In the extended configuration, the sleeve 506 extends through the first seal assembly 204a and at least partially into the second seal assembly 204b. Moreover, in the extended configuration, the bushing 508 translates or "telescopes" out of the sleeve and thereby penetrates the second seal assembly 204b. When in the extended configuration, the bushing 508 extends through the second seal assembly 204b and into the lumen 302 such that the lumen 302 fluidly communicates with the ambient environment via the passageways 512a,b. In the retracted configuration, the bushing 508 is received into the pathway 512a of the sleeve 506 and does not penetrate the second seal assembly 204b. Insufflation pressure will be maintained when the telescoping bushing assembly 502 is in the retracted configuration.

In the illustrated embodiment, the telescoping bushing assembly 502 also includes a seal 514, such as a diaphragm seal, annularly disposed within the passageway 512a at a proximal end thereof. The seal 514 is configured to sealingly engage the outer diameter of a surgical tool inserted therethrough, and may be made of a pliable or elastic material including those mentioned herein with respect to the seal assemblies 204a,b of FIGS. 2-3.

The telescoping bushing assembly 502 may also include one or more telescope seals 516a,b, such as annular elastomers, gaskets, or O-rings. The first telescope seal 516a is set within the passageway 512a of the sleeve 506 at a distal end thereof. The second telescope seal 516b is set within the passageway 512b of the bushing 508 at a distal end thereof. Either or both of the first and second telescope seals 516a,b may be made of a pliable or elastic material including those mentioned herein with respect to the seal assemblies 204a,b of FIGS. 2-3.

In the illustrated embodiment, the first telescope seal 516a abuts an outer periphery of the bushing 508 so as to "grip" and/or provide friction that resists axial translation of the bushing 508 along centerline A. The second telescope seal 516b may be configured to sealingly engage the outer surface of a surgical tool inserted through the passageway 512b. As discussed below, the second telescope seal 516b may also be configured to "grip" and otherwise provide a frictional engagement against the outer surface of the surgical tool as it is inserted therethrough, thereby distally extending or "carrying" the telescoping bushing 508 along centerline A.

Figures 6A, 6B:
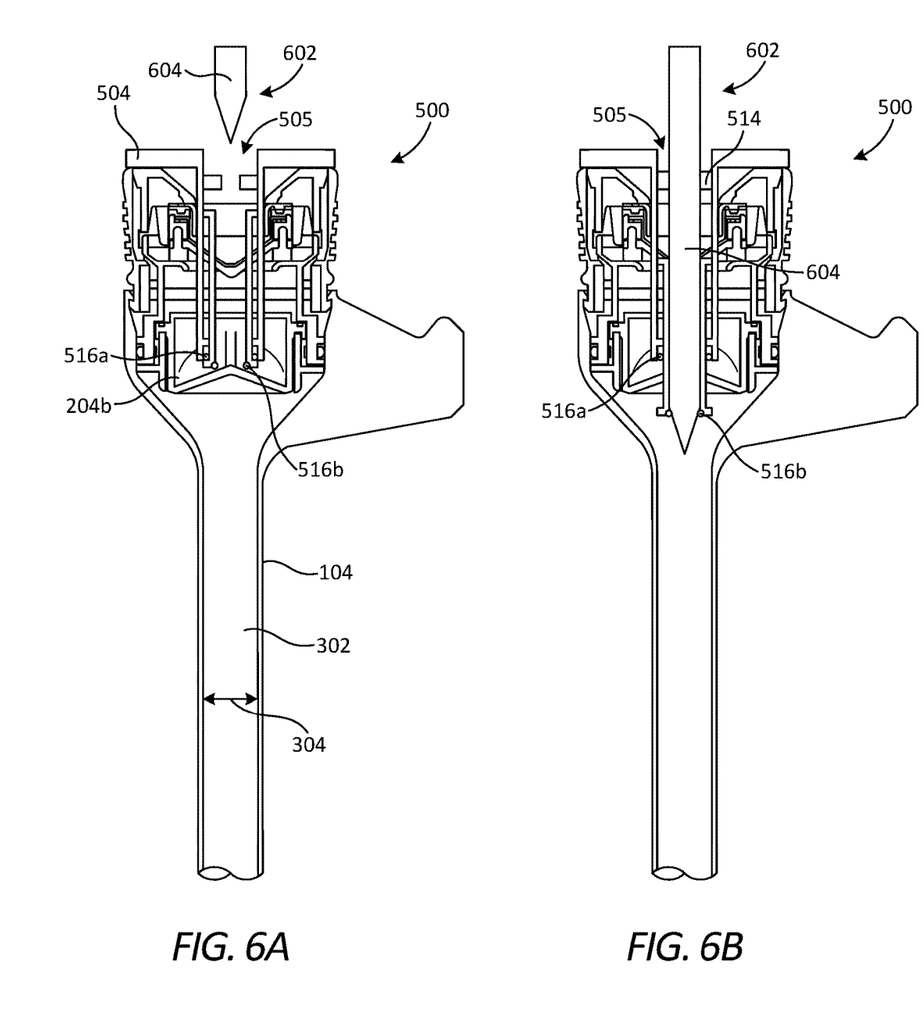
FIGS. 6A-6C are cross-sectional side views of the telescoping bushing assembly of FIGS. 5A and 5B depicting example operation.
Figure 6C:
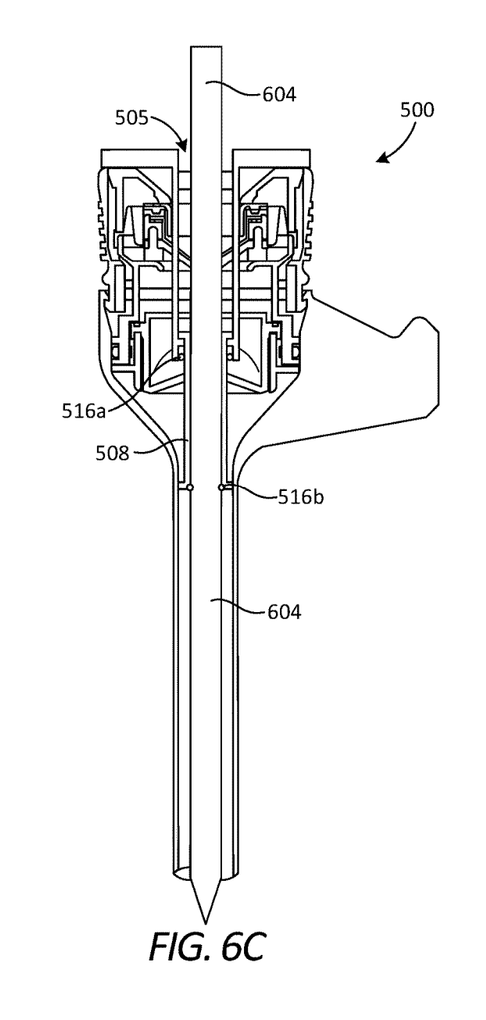

FIGS. 6A-6C depict an example operation of the trocar assembly 500 of FIGS. 5A-5B, according to one or more embodiments. As illustrated, the telescoping bushing assembly 502 is shown transitioning from the retracted configuration, as depicted in FIG. 6A, to an intermediate configuration, as shown in FIG. 6B, and to the extended configuration, as shown in FIG. 6C. As also illustrated, a surgical tool 602 is shown being extended into the trocar assembly 500. The surgical tool 602 includes a shaft 604 that penetrates the seal assemblies 204a,b and causes the telescoping bushing assembly 502 to transition between the retracted and extended configurations.

More specifically, FIGS. 6A-6C illustrate operation of the telescoping bushing assembly 502 when utilized with the surgical tool 602. As the shaft 604 enters the opening 505 of the ring 504, it passes through the seal 514 and the pathway 512a of the sleeve 506 and into the pathway 512b of the telescoping bushing 508. As the shaft 604 is driven through the pathway 512b of the telescoping bushing 508, it encounters the second telescope seal 516b that "grips" the outer surface of the shaft 604 such that the surgical tool 602 carries or extends the telescoping bushing 508 along centerline A, through second seal assembly 204b, and ultimately into its extended position.

Upon retraction of the surgical tool 602, the friction between the second telescope seal 516b and the shaft 604 of the surgical tool 602 retracts the telescoping bushing 508 in a proximal direction along centerline A past the second seal assembly 204b. In the illustrated embodiment, the shaft 604 of the surgical tool 602 will not be fully retracted from the passageway 512b of the bushing 508 until the bushing 508 is in its extreme distal orientation (FIG. 5A) such that seal assembly 204b is engaged or closed (i.e., with no portion of the surgical tool 602 extending there-through) to maintain insufflation pressure.

Embodiments disclosed herein include:

A. A trocar assembly that includes a housing that defines a working chamber, a cannula extending distally from the housing and defining a lumen that communicates with the working chamber, a seal cartridge at least partially arrangeable within the working chamber and including one or both of a proximal seal assembly and a distal seal assembly, the seal cartridge further including a bushing extending distally from a distal end of the seal cartridge and into the lumen, and a tertiary seal positioned within the working chamber distal to the seal cartridge, wherein the bushing extends through the tertiary seal when the seal cartridge is received within the working chamber.

B. A method of using a trocar assembly that includes insufflating a body cavity with the trocar assembly, the trocar assembly including a housing that defines a working chamber, and a cannula extending distally from the housing and defining a lumen that communicates with the working chamber, removing from the working chamber a first seal cartridge at least partially received within the working chamber, maintaining insufflation pressure within the body cavity with a tertiary seal positioned at a distal region of the working chamber, installing a second seal cartridge in the working chamber, the second seal cartridge including a bushing extending distally from a distal end of the seal cartridge, and penetrating the tertiary seal with the bushing as the second seal cartridge is extended into the working chamber.

C. A trocar assembly that includes a housing that defines a working chamber, a cannula extending distally from the housing and defining a lumen that communicates with the working chamber, a seal cartridge at least partially arrangeable within the working chamber and including a bushing extending distally into the lumen from a distal end of the seal cartridge and, and a tertiary seal positioned within a distal region of the working chamber and distal to the seal cartridge, wherein the bushing extends through the tertiary seal when the seal cartridge is received within the working chamber.

Each of embodiments A, B, and C may have one or more of the following additional elements in any combination: Element 1: wherein the tertiary seal is made of an elastic material selected from the group consisting of rubber, silicone, ethylene vinyl acetate, nylon, vinyl, spandex, polyurethane, polyethylene, polypropylene, polyisoprene, and any combination thereof. Element 2: wherein the bushing is attached to the distal end of the seal cartridge via an attachment means selected from the group consisting of one or more mechanical fasteners, a threaded engagement, welding, ultrasonic welding, brazing, an adhesive, an interference fit, a shrink fit, a mechanical attachment, and any combination thereof. Element 3: wherein the tertiary seal is disposed within a groove formed into a surface of the working chamber. Element 4: wherein the groove is located at a distal region of the working chamber. Element 5: wherein the tertiary seal is a duckbill seal. Element 6: wherein the bushing extends through the lumen and terminates at a distal end of the cannula. Element 7: wherein the bushing comprises a proximal portion that is configured to receive the distal seal assembly. Element 8: wherein the proximal portion comprises a frustoconical portion. Element 9: wherein the bushing comprises a proximal portion having a first diameter and a distal portion having a second diameter that is less than the first diameter. Element 10: wherein the bushing comprises a distal portion having an inner diameter that is less than a diameter of the lumen. Element 11: wherein insufflation pressure is maintained during removal of the seal cartridge from the working chamber with the tertiary seal.

Element 12: wherein the tertiary seal is disposed within a groove formed into a surface of the working chamber. Element 13: wherein the tertiary seal is a duckbill seal. Element 14: wherein the second seal cartridge includes one or both of a proximal seal assembly and a distal seal assembly arranged distally from the proximal seal assembly.

Element 15: wherein the tertiary seal is disposed within a groove formed into a surface of a distal region the working chamber. Element 16: wherein the tertiary seal is a duckbill seal. Element 17: wherein the seal cartridge further comprises one or both of a proximal seal assembly and a distal seal assembly arranged distally from the proximal seal assembly.

By way of non-limiting example, exemplary combinations applicable to A, B, and C include: Element 3 with Element 4; and Element 7 with Element 8.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an element closer to the surgeon or the robotic manipulator and the term "distal" refers to the position of an element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A trocar assembly, comprising:
   a housing that defines a working chamber;
   a cannula extending distally from the housing and defining a lumen that communicates with the working chamber;
   a seal cartridge at least partially arrangeable within the working chamber and including a proximal seal assembly and a distal seal assembly;
   a bushing secured to and extending distally from a distal end of the seal cartridge and having a proximal portion arranged within the working chamber and a distal portion extending into the lumen, wherein at least a portion of the distal seal assembly is received within the proximal portion; and
   a tertiary seal immovably secured to the housing within the working chamber distal to the seal cartridge, wherein the bushing extends through the tertiary seal when the seal cartridge is received within the working chamber.

2. The trocar assembly of claim 1, wherein the tertiary seal is made of an elastic material selected from the group consisting of rubber, silicone, ethylene vinyl acetate, nylon, vinyl, spandex, polyurethane, polyethylene, polypropylene, polyisoprene, and any combination thereof.

3. The trocar assembly of claim 1, wherein the bushing is attached to the distal end of the seal cartridge via an attachment means selected from the group consisting of one or more mechanical fasteners, a threaded engagement, welding, ultrasonic welding, brazing, an adhesive, an interference fit, a shrink fit, a mechanical attachment, and any combination thereof.

4. The trocar assembly of claim 1, wherein the tertiary seal is secured to the housing within a groove formed into a surface of the working chamber.

5. The trocar assembly of claim 4, wherein the groove is located at a distal region of the working chamber.

6. The trocar assembly of claim 1, wherein the tertiary seal is a duckbill seal.

7. The trocar assembly of claim 1, wherein the distal portion of the bushing extends through the lumen and terminates at a distal end of the cannula.

8. The trocar assembly of claim 1, wherein the proximal portion comprises a frustoconical portion.

9. The trocar assembly of claim 1, wherein the proximal portion exhibits a first inner diameter that receives the distal seal assembly and the distal portion exhibits a second inner diameter that is less than the first inner diameter.

10. The trocar assembly of claim 1, wherein the distal portion exhibits an inner diameter that is less than a diameter of the lumen.

11. The trocar assembly of claim 1, wherein insufflation pressure is maintained during removal of the seal cartridge from the working chamber with the tertiary seal.

12. The trocar assembly of claim 1, wherein the seal cartridge and the bushing are immovably secured to the housing when received within the working chamber.

13. A method of using a trocar assembly, comprising:
    insufflating a body cavity with the trocar assembly, the trocar assembly including a housing that defines a working chamber, and a cannula extending distally from the housing and defining a lumen that communicates with the working chamber;
    removing from the working chamber a first seal cartridge at least partially received within the working chamber;
    maintaining insufflation pressure within the body cavity with a tertiary seal immovably secured to the housing at a distal region of the working chamber;
    installing a second seal cartridge in the working chamber, the second seal cartridge including:
      a bushing secured to and extending distally from a distal end of the seal cartridge and having a proximal portion arranged within the working chamber and a distal portion extending into the lumen; and
      a distal seal assembly at least partially received within the proximal portion of the bushing; and
    penetrating the tertiary seal with the distal portion of the bushing as the second seal cartridge is extended into the working chamber.

14. The method of claim 13, wherein the tertiary seal is secured to the housing within a groove formed into a surface of the working chamber.

15. The method of claim 13, wherein the tertiary seal is a duckbill seal.

16. The method of claim 13, wherein the second seal cartridge further includes a proximal seal assembly arranged proximally from the distal seal assembly.

17. A trocar assembly, comprising:
    a housing that defines a working chamber;
    a cannula extending distally from the housing and defining a lumen that communicates with the working chamber;
    a seal cartridge at least partially arrangeable within the working chamber and including a bushing immovably secured to and extending distally into the lumen from a distal end of the seal cartridge, wherein the seal cartridge is immovably secured to the housing when received within the working chamber; and a tertiary seal immovably secured to the housing within a distal region of the working chamber and distal to the seal cartridge, wherein the bushing extends through the tertiary seal when the seal cartridge is received within the working chamber.

18. The trocar assembly of claim 17, wherein the tertiary seal is secured to the housing within a groove formed into a surface of a distal region the working chamber.

19. The trocar assembly of claim 17, wherein the tertiary seal is a duckbill seal.

20. The trocar assembly of claim 17, wherein the seal cartridge further comprises one or both of a proximal seal assembly and a distal seal assembly arranged distally from the proximal seal assembly, and wherein at least a portion of the distal seal assembly is received within a proximal portion of the bushing.

* * * * *